(12) United States Patent
Bujard et al.

(10) Patent No.: US 8,318,185 B2
(45) Date of Patent: Nov. 27, 2012

(54) RECOMBINANT MALARIA VACCINE

(75) Inventors: Hermann Bujard, Heidelberg (DE); Rolf Lutz, Rülzheim (DE); Christian Kauth, Heidelberg (DE); Christian Epp, Heidelberg (DE); Ute Wöhlbier, Seattle, WA (US)

(73) Assignee: Ruprecht-Karls-Universität Heidelberg, Heidelberg (DE)

( * ) Notice: Subject to any disclaimer, the term of this patent is extended or adjusted under 35 U.S.C. 154(b) by 119 days.

(21) Appl. No.: 12/523,023

(22) PCT Filed: Jan. 11, 2008

(86) PCT No.: PCT/EP2008/000203
§ 371 (c)(1),
(2), (4) Date: Jul. 20, 2010

(87) PCT Pub. No.: WO2008/086984
PCT Pub. Date: Jul. 24, 2008

(65) Prior Publication Data
US 2010/0297163 A1    Nov. 25, 2010

(30) Foreign Application Priority Data

Jan. 15, 2007   (EP) ..................... 07000710

(51) Int. Cl.
*A61K 39/015* (2006.01)
*C12P 21/06* (2006.01)
(52) U.S. Cl. .................. 424/272.1; 424/192.1; 435/69.1
(58) Field of Classification Search ........................ None
See application file for complete search history.

(56) References Cited

U.S. PATENT DOCUMENTS 6,933,130 B1 *   8/2005   Bujard et al. ................ 435/69.1

FOREIGN PATENT DOCUMENTS

| EP | 1 637 602 A1 | 2/1997 |
| WO | WO 98/14583 A2 | 4/1998 |
| WO | WO 2004038024 A1 | 5/2004 |

OTHER PUBLICATIONS

Kauth et al. The merozoite surface protein 1 complex of human malaria parasite *Plasmodium falciparum*: interactions and arrangements of subunits. J Biol Chem. Jun. 20, 2003;278(25):22257-64.
Woehlbier, et al. Analysis of antibodies directed against merozoite surface protein 1 of the human malaria parasite *Plasmodium falciparum*. Infect Immun. Feb. 2006:74(2):1313-22.

* cited by examiner

*Primary Examiner* — Padma Baskar
(74) *Attorney, Agent, or Firm* — Paula A. Borden, Ph.D.; Bozicevic, Field & Francis LLP.

(57) ABSTRACT

The present invention refers to a recombinant malaria vaccine and a method for its manufacture.

23 Claims, 4 Drawing Sheets

SEQUENCES

SEQ ID NO: 1:

MSP-1F  AA 1686

MSP-1F 83/30  AA 872

MKIIFFLCSFLFFIINTQC<u>VTHESYQEL</u>VKKLEALEDAVLTGYSLFQKEKMVLKDGANTQVVAKPADAVSTQ
SAKNPPGATVPSGTASTKGAIRSPGAANPSDDSSDSDAKSYADLKHRVQNYLFTIKELKYPELFDLTNHML
TLCDNIHGFKYLIDGYEEINELLYKLNFYFDLLRAKLNDVCANDYCQIPFNLKIRANELDVLKKLVFGYRKPL
DFIKDNVGKMEDYIKKNKTTIANINELIEGSKKTIDQNKNADNEEGKKKLYQAQYDLFIYNKQLQEAHNLISV
LEKRIDTLKKNENIKKLLEDIDKIKIDAEKPTTGVNQILSLRLEKESRHEEKIKEIAKTIKFNIDRLFTDPLELEYY
LREKNKKVDVTPKSQDPTKSVQIPKVPYPNGIVYPLPLTDIHNSLAADNDKNSYGDLMNPHTKEKINEKIIT
DNKERKIFINNIKKQIDLEEKNINHTKEQNKKLLEDYEKSKKDYEELLEKFYEMKFNNNFNKDVVDKIFSARY
TYNVEKQRYNNKFSSSNNSVYNVQKLK*KALSYLEDYSL*RKGISEKDFNHYYTLKTGLEADIKKLTEEIKSS
ENKILEKNFKGLTHSANASLEVSDIVKLQVQKVLLIKKIEDLRKIELFLKNAQLKDSIHVPNIYKPQNKPEPYY
LIVLKKEVDKLKEFIPKVKDMLKKEQAVLSSITQPLVAASETTEDGGHSTHTLSQSGETEVTEETEETVGHT
TTVTITLPPKEVKVVENSIEHKSNDNSQALTKTVYLKKLDEFLTKSYICHKYILVSNSSMDQKLLEVYNLTPE
ENELKSCDRLDLLFNIQNNIPAMYSLYDSMNNDLQHLFFELYQKEMIYYLHKLKEENHIKKLLEEPKQITG

SEQ ID NO: 2:

MSP-1D 83/30 → AA 893 (2 AA substitutions at position 611E → K and 866Q → H)

M<u>VTHESYQEL</u>VKKLEALEDAVLTGYSLFQKEKMVLNEEEITTKGASAQSGASAQSGASAQSGASAQSGA
SAQSGASAQSGTSGPSGPSGTSPSSRSNTLPRSNTSSGASPPADASDSDAKSYADLKHRVRNYLFTIKE
LKYPELFDLTNHMLTLCDNIHGFKYLIDGYEEINELLYKLNFYFDLLRAKLNDVCANDYCQIPFNLKIRANEL
DVLKKLVFGYRKPLDNIKDNVGKMEDYIKKNKTTIANINELIEGSKKTIDQNKNADNEEGKKKLYQAQYDLSI
YNKQLEEAHNLISVLEKRIDTLKKNENIKKLLDKINEIKNPPPANSGNTPNTLLDKNKKIEEHEEKIKEIAKTIK
FNIDSLFTDPLELEYYLREKNKKVDVTPKSQDPTKSVQIPKVPYPNGIVYPLPLTDIHNSLAADNDKNSYGD
LMNPHTKEKINEKIITDNKERKIFINNIKKKIDLEEKNINHTKEQNKKLLEDYEKSKKDYEELLEKFYEMKFNN
NFDKDVVDKIFSARYTYNVEKQRYNNKFSSSNNSVYNVQKLK*KALSYLEDYSL*RKGISEKDFNHYYTLKT
GLEADIKKLTEEIKSSENKILEKNFKGLTHSANGSLK
(VSDIVKLQVQKVLLIKKIEDLRKIELFLKNAQLKDSIHVPNIYKPQNKPEPYYLIVLKKEVDKLKEFIPKVKDM
LKKEQAVLSSITQPLVAASETTEDGGHSTHTLSQSGETEVTEETEETEETVGHTTTVTITLPPTQPSPPKEV
KVVENSIEHKSNDNSQALTKTVYLKKLDEFLTKSYICHKYILVSNSSMDQKLLEVYNLTPEEENELKSCDPL
DLLFNIQNNIPAMYSLYDSMNNDLQHLFFELYQKEMIYYLHKLKEENHIKKLLEEQKQITGTS

Figure 3 (Continued)

SEQ ID NO: 3:

MSP 1F 38/42      AA 808

T*SSTSSPGNTTV*NTAQSATHSNSQNQQSNASSTNTQNGVAVSSGPAVVEESHDPLTVLSISNDLKGIVSL
LNLGNKTKVPNPLTISTTEMEKFYENILKIMIPIFNDDIKQFVKSNSKVITGLTETQKNALNDEIKKLKDTLQLS
FDLYNKYKLKLDRLFNKKKELGQDK*MQIKKLTLLK*EQLESKLNSLNNPHNVLQNFSVFFNKKKEAEIAETE
NTLENTKILLKHYKGLVKYYNGESSPLKTLSEVSIQTEDNYANLEKFRVLSKIDGKLNDNLHLGKKKLSFLSS
GLHHLITELKEVIKNKNYTGNSPSENNKKVNEALKSYENFLPEAKVTTVVTPPQPDVTPSPLSVRVSGSSG
STKEETQIPTSGSLLTELQQVVQLQNYDEEDDSLVVLPIFGESEDNDEYLDQVVTGEAISVTMDNILSGFEN
EYDVIYLKPLAGVYRSLKKQIEKNIFTFNLNLNDILNSRLKKRKYFLDVLESDLMQFKHISSNEYIIEDSFKLLN
SEQKNTLLKSYKYIKESVENDIKFAQEGISYYEKVLAKYKDDLESIKKVIKEEKEFPSSPPTTPPSPAKTDEQ
KKESKFLPFLTNIETLYNNLVNKIDDYLINLKAKINDCNVEKDEAHVKITKLSDLKAIDDKIDLFKNPYDFEAIK
KLINDDTKKDMLGKLLSTGLVQNFPNTIISKLIEGKFQDMLNISQHQCVKKQCPQNSGCFRHLDEREECKC
LLNYKQEGDKCVENPNPTCNENNGGCDADAKCTEEDSGSNGKKITCECTKPDSYPLFDGIFCSSSNFLGI
SFLLILMLILYS

SEQ ID NO: 4:

MSP-1D 38/42      AA 794

MS*STSSPGNTTV*NTAQSATHSNSQNQQSNASSTNTQNGVAVSSGPAVVEESHDPLTVLSISNDLKGIVSL
LNLGNKTKVPNPLTISTTEMEKFYENILKNNDTYFNDDIKQFVKSNSKVITGLTETQKNALNDEIKKLKDTLQ
LSFDLYNKYKLKLDRLFNKKKELGQDK*MQIKKLTLLK*EQLESKLNSLNNPHNVLQNFSVFFNKKKEAEIAE
TENTLENTKILLKHYKGLVKYYNGESSPLKTLSEVSIQTEDNYANLEKFRVLSKIDGKLNDNLHLGKKKLSFL
SSGLHHLITELKEVIKNKNYTGNSPSENNKKVNEALKSYENFLPEAKVTTVVTPPQPDVTPSPLSVRVSGS
SGSTKEETQIPTSGSLLTELQQVVQLQNYDEEDDSLVVLPIFGESEDNDEYLDQVVTGEAISVTMDNILSG
FENEYDVIYLKPLAGVYRSLKKQIEKNIFTFNLNLNDILNSRLKKRKYFLDVLESDLMQFKHISSNEYIIEDSF
KLLNSEQKNTLLKSYKYIKESVENDIKFAQEGISYYEKVLAKYKDDLESIKKVIKEEKEKFPSSPPTTPPSPA
KTDEQKKESKFLPFLTNIETLYNNLVNKIDDYLINLKAKINDCNVEKDEAHVKITKLSDLKAIDDKIDLFKNPY
DFEAIKKLINDDTKKDMLGKLLSTGLVQNFPNTIISKLIEGKFQDMLNISQHQCVKKQCPENSGCFRHLDER
EECKCLLNYKQEGDKCVENPNPTCNENNGGCDADATCTEEDSGSSRKKITCECTKPDSYPLFDGIFCSS
SNV*

SEQUENCE LISTING

```
<160> NUMBER OF SEQ ID NOS: 4

<210> SEQ ID NO 1
<211> LENGTH: 872
<212> TYPE: PRT
<213> ORGANISM: P. falciparum

<400> SEQUENCE: 1

Met Lys Ile Ile Phe Phe Leu Cys Ser Phe Leu Phe Phe Ile Ile Asn
 1               5                   10                  15

Thr Gln Cys Val Thr His Glu Ser Tyr Gln Glu Leu Val Lys Lys Leu
            20                  25                  30

Glu Ala Leu Glu Asp Ala Val Leu Thr Gly Tyr Ser Leu Phe Gln Lys
        35                  40                  45

Glu Lys Met Val Leu Lys Asp Gly Ala Asn Thr Gln Val Val Ala Lys
```

```
                50                  55                  60
Pro Ala Asp Ala Val Ser Thr Gln Ser Ala Lys Asn Pro Pro Gly Ala
65                  70                  75                  80

Thr Val Pro Ser Gly Thr Ala Ser Thr Lys Gly Ala Ile Arg Ser Pro
                85                  90                  95

Gly Ala Ala Asn Pro Ser Asp Asp Ser Ser Asp Ser Asp Ala Lys Ser
            100                 105                 110

Tyr Ala Asp Leu Lys His Arg Val Gln Asn Tyr Leu Phe Thr Ile Lys
            115                 120                 125

Glu Leu Lys Tyr Pro Glu Leu Phe Asp Leu Thr Asn His Met Leu Thr
130                 135                 140

Leu Cys Asp Asn Ile His Gly Phe Lys Tyr Leu Ile Asp Gly Tyr Glu
145                 150                 155                 160

Glu Ile Asn Glu Leu Leu Tyr Lys Leu Asn Phe Tyr Phe Asp Leu Leu
                165                 170                 175

Arg Ala Lys Leu Asn Asp Val Cys Ala Asn Asp Tyr Cys Gln Ile Pro
            180                 185                 190

Phe Asn Leu Lys Ile Arg Ala Asn Glu Leu Asp Val Leu Lys Lys Leu
            195                 200                 205

Val Phe Gly Tyr Arg Lys Pro Leu Asp Phe Ile Lys Asp Asn Val Gly
210                 215                 220

Lys Met Glu Asp Tyr Ile Lys Lys Asn Lys Thr Thr Ile Ala Asn Ile
225                 230                 235                 240

Asn Glu Leu Ile Glu Gly Ser Lys Lys Thr Ile Asp Gln Asn Lys Asn
                245                 250                 255

Ala Asp Asn Glu Glu Gly Lys Lys Lys Leu Tyr Gln Ala Gln Tyr Asp
            260                 265                 270

Leu Phe Ile Tyr Asn Lys Gln Leu Gln Glu Ala His Asn Leu Ile Ser
            275                 280                 285

Val Leu Glu Lys Arg Ile Asp Thr Leu Lys Lys Asn Glu Asn Ile Lys
290                 295                 300

Lys Leu Leu Glu Asp Ile Asp Lys Ile Lys Ile Asp Ala Glu Lys Pro
305                 310                 315                 320

Thr Thr Gly Val Asn Gln Ile Leu Ser Leu Arg Leu Glu Lys Glu Ser
                325                 330                 335

Arg His Glu Glu Lys Ile Lys Glu Ile Ala Lys Thr Ile Lys Phe Asn
            340                 345                 350

Ile Asp Arg Leu Phe Thr Asp Pro Leu Glu Leu Glu Tyr Tyr Leu Arg
            355                 360                 365

Glu Lys Asn Lys Lys Val Asp Val Thr Pro Lys Ser Gln Asp Pro Thr
370                 375                 380

Lys Ser Val Gln Ile Pro Lys Val Pro Tyr Pro Asn Gly Ile Val Tyr
385                 390                 395                 400

Pro Leu Pro Leu Thr Asp Ile His Asn Ser Leu Ala Ala Asp Asn Asp
                405                 410                 415

Lys Asn Ser Tyr Gly Asp Leu Met Asn Pro His Thr Lys Glu Lys Ile
            420                 425                 430

Asn Glu Lys Ile Ile Thr Asp Asn Lys Glu Arg Lys Ile Phe Ile Asn
            435                 440                 445

Asn Ile Lys Lys Gln Ile Asp Leu Glu Glu Lys Asn Ile Asn His Thr
            450                 455                 460

Lys Glu Gln Asn Lys Lys Leu Leu Glu Asp Tyr Glu Lys Ser Lys Lys
465                 470                 475                 480
```

```
Asp Tyr Glu Glu Leu Leu Glu Lys Phe Tyr Glu Met Lys Phe Asn Asn
                485                 490                 495

Asn Phe Asn Lys Asp Val Val Asp Lys Ile Phe Ser Ala Arg Tyr Thr
            500                 505                 510

Tyr Asn Val Glu Lys Gln Arg Tyr Asn Asn Lys Phe Ser Ser Ser Asn
        515                 520                 525

Asn Ser Val Tyr Asn Val Gln Lys Leu Lys Lys Ala Leu Ser Tyr Leu
    530                 535                 540

Glu Asp Tyr Ser Leu Arg Lys Gly Ile Ser Glu Lys Asp Phe Asn His
545                 550                 555                 560

Tyr Tyr Thr Leu Lys Thr Gly Leu Glu Ala Asp Ile Lys Lys Leu Thr
                565                 570                 575

Glu Glu Ile Lys Ser Ser Glu Asn Lys Ile Leu Glu Lys Asn Phe Lys
            580                 585                 590

Gly Leu Thr His Ser Ala Asn Ala Ser Leu Glu Val Ser Asp Ile Val
        595                 600                 605

Lys Leu Gln Val Gln Lys Val Leu Leu Ile Lys Lys Ile Glu Asp Leu
    610                 615                 620

Arg Lys Ile Glu Leu Phe Leu Lys Asn Ala Gln Leu Lys Asp Ser Ile
625                 630                 635                 640

His Val Pro Asn Ile Tyr Lys Pro Gln Asn Lys Pro Glu Pro Tyr Tyr
                645                 650                 655

Leu Ile Val Leu Lys Lys Glu Val Asp Lys Leu Lys Glu Phe Ile Pro
            660                 665                 670

Lys Val Lys Asp Met Leu Lys Lys Glu Gln Ala Val Leu Ser Ser Ile
        675                 680                 685

Thr Gln Pro Leu Val Ala Ala Ser Glu Thr Thr Glu Asp Gly Gly His
    690                 695                 700

Ser Thr His Thr Leu Ser Gln Ser Gly Glu Thr Glu Val Thr Glu Glu
705                 710                 715                 720

Thr Glu Glu Thr Val Gly His Thr Thr Thr Val Ile Thr Leu Pro
                725                 730                 735

Pro Lys Glu Val Lys Val Val Glu Asn Ser Ile Glu His Lys Ser Asn
            740                 745                 750

Asp Asn Ser Gln Ala Leu Thr Lys Thr Val Tyr Leu Lys Lys Leu Asp
        755                 760                 765

Glu Phe Leu Thr Lys Ser Tyr Ile Cys His Lys Tyr Ile Leu Val Ser
    770                 775                 780

Asn Ser Ser Met Asp Gln Lys Leu Leu Glu Val Tyr Asn Leu Thr Pro
785                 790                 795                 800

Glu Glu Asn Glu Leu Lys Ser Cys Asp Arg Leu Asp Leu Leu Phe Asn
                805                 810                 815

Ile Gln Asn Asn Ile Pro Ala Met Tyr Ser Leu Tyr Asp Ser Met Asn
            820                 825                 830

Asn Asp Leu Gln His Leu Phe Phe Glu Leu Tyr Gln Lys Glu Met Ile
        835                 840                 845

Tyr Tyr Leu His Lys Leu Lys Glu Asn His Ile Lys Lys Leu Leu
    850                 855                 860

Glu Glu Pro Lys Gln Ile Thr Gly
865                 870

<210> SEQ ID NO 2
<211> LENGTH: 893
<212> TYPE: PRT
<213> ORGANISM: P. falciparum
```

```
<400> SEQUENCE: 2

Met Val Thr His Glu Ser Tyr Gln Glu Leu Val Lys Lys Leu Glu Ala
  1               5                  10                  15

Leu Glu Asp Ala Val Leu Thr Gly Tyr Ser Leu Phe Gln Lys Glu Lys
                 20                  25                  30

Met Val Leu Asn Glu Glu Ile Thr Thr Lys Gly Ala Ser Ala Gln
             35                  40                  45

Ser Gly Ala Ser Ala Gln Ser Gly Ala Ser Ala Gln Ser Gly Ala Ser
     50                  55                  60

Ala Gln Ser Gly Ala Ser Ala Gln Ser Gly Ala Ser Ala Gln Ser Gly
 65                  70                  75                  80

Thr Ser Gly Pro Ser Gly Pro Ser Gly Thr Ser Pro Ser Ser Arg Ser
                 85                  90                  95

Asn Thr Leu Pro Arg Ser Asn Thr Ser Ser Gly Ala Ser Pro Pro Ala
                100                 105                 110

Asp Ala Ser Asp Ser Asp Ala Lys Ser Tyr Ala Asp Leu Lys His Arg
                115                 120                 125

Val Arg Asn Tyr Leu Phe Thr Ile Lys Glu Leu Lys Tyr Pro Glu Leu
                130                 135                 140

Phe Asp Leu Thr Asn His Met Leu Thr Leu Cys Asp Asn Ile His Gly
145                 150                 155                 160

Phe Lys Tyr Leu Ile Asp Gly Tyr Glu Glu Ile Asn Glu Leu Leu Tyr
                165                 170                 175

Lys Leu Asn Phe Tyr Phe Asp Leu Leu Arg Ala Lys Leu Asn Asp Val
                180                 185                 190

Cys Ala Asn Asp Tyr Cys Gln Ile Pro Phe Asn Leu Lys Ile Arg Ala
                195                 200                 205

Asn Glu Leu Asp Val Leu Lys Lys Leu Val Phe Gly Tyr Arg Lys Pro
                210                 215                 220

Leu Asp Asn Ile Lys Asp Asn Val Gly Lys Met Glu Asp Tyr Ile Lys
225                 230                 235                 240

Lys Asn Lys Thr Thr Ile Ala Asn Ile Asn Glu Leu Ile Glu Gly Ser
                245                 250                 255

Lys Lys Thr Ile Asp Gln Asn Lys Asn Ala Asp Asn Glu Glu Gly Lys
                260                 265                 270

Lys Lys Leu Tyr Gln Ala Gln Tyr Asp Leu Ser Ile Tyr Asn Lys Gln
                275                 280                 285

Leu Glu Glu Ala His Asn Leu Ile Ser Val Leu Glu Lys Arg Ile Asp
                290                 295                 300

Thr Leu Lys Lys Asn Glu Asn Ile Lys Lys Leu Leu Asp Lys Ile Asn
305                 310                 315                 320

Glu Ile Lys Asn Pro Pro Ala Asn Ser Gly Asn Thr Pro Asn Thr
                325                 330                 335

Leu Leu Asp Lys Asn Lys Lys Ile Glu Glu His Glu Glu Lys Ile Lys
                340                 345                 350

Glu Ile Ala Lys Thr Ile Lys Phe Asn Ile Asp Ser Leu Phe Thr Asp
                355                 360                 365

Pro Leu Glu Leu Glu Tyr Tyr Leu Arg Glu Lys Asn Lys Lys Val Asp
                370                 375                 380

Val Thr Pro Lys Ser Gln Asp Pro Thr Lys Ser Val Gln Ile Pro Lys
385                 390                 395                 400

Val Pro Tyr Pro Asn Gly Ile Val Tyr Pro Leu Pro Leu Thr Asp Ile
                405                 410                 415
```

-continued

His Asn Ser Leu Ala Ala Asp Asn Asp Lys Asn Ser Tyr Gly Asp Leu
        420                 425                 430

Met Asn Pro His Thr Lys Glu Lys Ile Asn Glu Lys Ile Ile Thr Asp
            435                 440                 445

Asn Lys Glu Arg Lys Ile Phe Ile Asn Asn Ile Lys Lys Lys Ile Asp
        450                 455                 460

Leu Glu Glu Lys Asn Ile Asn His Thr Lys Glu Gln Asn Lys Lys Leu
465                 470                 475                 480

Leu Glu Asp Tyr Glu Lys Ser Lys Lys Asp Tyr Glu Leu Leu Glu
            485                 490                 495

Lys Phe Tyr Glu Met Lys Phe Asn Asn Asn Phe Asp Lys Asp Val Val
                500                 505                 510

Asp Lys Ile Phe Ser Ala Arg Tyr Thr Tyr Asn Val Glu Lys Gln Arg
            515                 520                 525

Tyr Asn Asn Lys Phe Ser Ser Ser Asn Asn Ser Val Tyr Asn Val Gln
                530                 535                 540

Lys Leu Lys Lys Ala Leu Ser Tyr Leu Glu Asp Tyr Ser Leu Arg Lys
545                 550                 555                 560

Gly Ile Ser Glu Lys Asp Phe Asn His Tyr Tyr Thr Leu Lys Thr Gly
            565                 570                 575

Leu Glu Ala Asp Ile Lys Lys Leu Thr Glu Glu Ile Lys Ser Ser Glu
            580                 585                 590

Asn Lys Ile Leu Glu Lys Asn Phe Lys Gly Leu Thr His Ser Ala Asn
        595                 600                 605

Gly Ser Leu Lys Val Ser Asp Ile Val Lys Leu Gln Val Gln Lys Val
        610                 615                 620

Leu Leu Ile Lys Lys Ile Glu Asp Leu Arg Lys Ile Glu Leu Phe Leu
625                 630                 635                 640

Lys Asn Ala Gln Leu Lys Asp Ser Ile His Val Pro Asn Ile Tyr Lys
            645                 650                 655

Pro Gln Asn Lys Pro Glu Pro Tyr Tyr Leu Ile Val Leu Lys Lys Glu
            660                 665                 670

Val Asp Lys Leu Lys Glu Phe Ile Pro Lys Val Lys Asp Met Leu Lys
        675                 680                 685

Lys Glu Gln Ala Val Leu Ser Ser Ile Thr Gln Pro Leu Val Ala Ala
        690                 695                 700

Ser Glu Thr Thr Glu Asp Gly Gly His Ser Thr His Thr Leu Ser Gln
705                 710                 715                 720

Ser Gly Glu Thr Glu Val Thr Glu Glu Thr Glu Thr Glu Glu Thr
                725                 730                 735

Val Gly His Thr Thr Thr Val Thr Ile Thr Leu Pro Pro Thr Gln Pro
            740                 745                 750

Ser Pro Pro Lys Glu Val Lys Val Val Glu Asn Ser Ile Glu His Lys
        755                 760                 765

Ser Asn Asp Asn Ser Gln Ala Leu Thr Lys Thr Val Tyr Leu Lys Lys
        770                 775                 780

Leu Asp Glu Phe Leu Thr Lys Ser Tyr Ile Cys His Lys Tyr Ile Leu
785                 790                 795                 800

Val Ser Asn Ser Ser Met Asp Gln Lys Leu Leu Glu Val Tyr Asn Leu
                805                 810                 815

Thr Pro Glu Glu Glu Asn Glu Leu Lys Ser Cys Asp Pro Leu Asp Leu
            820                 825                 830

Leu Phe Asn Ile Gln Asn Asn Ile Pro Ala Met Tyr Ser Leu Tyr Asp

-continued

```
                835                 840                 845
Ser Met Asn Asp Leu Gln His Leu Phe Glu Leu Tyr Gln Lys
        850                 855                 860

Glu Met Ile Tyr Tyr Leu His Lys Leu Lys Glu Asn His Ile Lys
865                 870                 875                 880

Lys Leu Leu Glu Glu Gln Lys Gln Ile Thr Gly Thr Ser
                885                 890

<210> SEQ ID NO 3
<211> LENGTH: 808
<212> TYPE: PRT
<213> ORGANISM: P. falciparum

<400> SEQUENCE: 3

Thr Ser Ser Thr Ser Ser Pro Gly Asn Thr Val Asn Thr Ala Gln
1               5                   10                  15

Ser Ala Thr His Ser Asn Ser Gln Asn Gln Gln Ser Asn Ala Ser Ser
            20                  25                  30

Thr Asn Thr Gln Asn Gly Val Ala Val Ser Ser Gly Pro Ala Val Val
        35                  40                  45

Glu Glu Ser His Asp Pro Leu Thr Val Leu Ser Ile Ser Asn Asp Leu
50                  55                  60

Lys Gly Ile Val Ser Leu Leu Asn Leu Gly Asn Lys Thr Lys Val Pro
65                  70                  75                  80

Asn Pro Leu Thr Ile Ser Thr Thr Glu Met Glu Lys Phe Tyr Glu Asn
            85                  90                  95

Ile Leu Lys Ile Met Ile Pro Ile Phe Asn Asp Asp Ile Lys Gln Phe
            100                 105                 110

Val Lys Ser Asn Ser Lys Val Ile Thr Gly Leu Thr Glu Thr Gln Lys
            115                 120                 125

Asn Ala Leu Asn Asp Glu Ile Lys Lys Leu Lys Asp Thr Leu Gln Leu
130                 135                 140

Ser Phe Asp Leu Tyr Asn Lys Tyr Lys Leu Lys Leu Asp Arg Leu Phe
145                 150                 155                 160

Asn Lys Lys Lys Glu Leu Gly Gln Asp Lys Met Gln Ile Lys Lys Leu
            165                 170                 175

Thr Leu Leu Lys Glu Gln Leu Glu Ser Lys Leu Asn Ser Leu Asn Asn
            180                 185                 190

Pro His Asn Val Leu Gln Asn Phe Ser Val Phe Asn Lys Lys Lys
            195                 200                 205

Glu Ala Glu Ile Ala Glu Thr Glu Asn Thr Leu Glu Asn Thr Lys Ile
210                 215                 220

Leu Leu Lys His Tyr Lys Gly Leu Val Lys Tyr Tyr Asn Gly Glu Ser
225                 230                 235                 240

Ser Pro Leu Lys Thr Leu Ser Glu Val Ser Ile Gln Thr Glu Asp Asn
            245                 250                 255

Tyr Ala Asn Leu Glu Lys Phe Arg Val Leu Ser Lys Ile Asp Gly Lys
            260                 265                 270

Leu Asn Asp Asn Leu His Leu Gly Lys Lys Leu Ser Phe Leu Ser
            275                 280                 285

Ser Gly Leu His His Leu Ile Thr Glu Leu Lys Glu Val Ile Lys Asn
            290                 295                 300

Lys Asn Tyr Thr Gly Asn Ser Pro Ser Glu Asn Asn Lys Lys Val Asn
305                 310                 315                 320

Glu Ala Leu Lys Ser Tyr Glu Asn Phe Leu Pro Glu Ala Lys Val Thr
```

```
                        325                 330                 335
Thr Val Val Thr Pro Pro Gln Pro Asp Val Thr Pro Ser Pro Leu Ser
                340                 345                 350
Val Arg Val Ser Gly Ser Ser Gly Ser Thr Lys Glu Glu Thr Gln Ile
                355                 360                 365
Pro Thr Ser Gly Ser Leu Leu Thr Glu Leu Gln Gln Val Val Gln Leu
370                 375                 380
Gln Asn Tyr Asp Glu Glu Asp Asp Ser Leu Val Val Leu Pro Ile Phe
385                 390                 395                 400
Gly Glu Ser Glu Asp Asn Asp Glu Tyr Leu Asp Gln Val Val Thr Gly
                405                 410                 415
Glu Ala Ile Ser Val Thr Met Asp Asn Ile Leu Ser Gly Phe Glu Asn
                420                 425                 430
Glu Tyr Asp Val Ile Tyr Leu Lys Pro Leu Ala Gly Val Tyr Arg Ser
                435                 440                 445
Leu Lys Lys Gln Ile Glu Lys Asn Ile Phe Thr Phe Asn Leu Asn Leu
                450                 455                 460
Asn Asp Ile Leu Asn Ser Arg Leu Lys Lys Arg Lys Tyr Phe Leu Asp
465                 470                 475                 480
Val Leu Glu Ser Asp Leu Met Gln Phe Lys His Ile Ser Ser Asn Glu
                485                 490                 495
Tyr Ile Ile Glu Asp Ser Phe Lys Leu Leu Asn Ser Glu Gln Lys Asn
                500                 505                 510
Thr Leu Leu Lys Ser Tyr Lys Tyr Ile Lys Glu Ser Val Gly Asn Asp
                515                 520                 525
Ile Lys Phe Ala Gln Glu Gly Ile Ser Tyr Tyr Glu Lys Val Leu Ala
                530                 535                 540
Lys Tyr Lys Asp Asp Leu Glu Ser Ile Lys Lys Val Ile Lys Glu Glu
545                 550                 555                 560
Lys Glu Phe Pro Ser Ser Pro Pro Thr Thr Pro Pro Ser Pro Ala Lys
                565                 570                 575
Thr Asp Glu Gln Lys Lys Glu Ser Lys Phe Leu Pro Phe Leu Thr Asn
                580                 585                 590
Ile Glu Thr Leu Tyr Asn Asn Leu Val Asn Lys Ile Asp Asp Tyr Leu
                595                 600                 605
Ile Asn Leu Lys Ala Lys Ile Asn Asp Cys Asn Val Glu Lys Asp Glu
                610                 615                 620
Ala His Val Lys Ile Thr Lys Leu Ser Asp Leu Lys Ala Ile Asp Asp
625                 630                 635                 640
Lys Ile Asp Leu Phe Lys Asn Pro Tyr Asp Phe Glu Ala Ile Lys Lys
                645                 650                 655
Leu Ile Asn Asp Asp Thr Lys Lys Asp Met Leu Gly Lys Leu Leu Ser
                660                 665                 670
Thr Gly Leu Val Gln Asn Phe Pro Asn Thr Ile Ile Ser Lys Leu Ile
                675                 680                 685
Glu Gly Lys Phe Gln Asp Met Leu Asn Ile Ser Gln His Gln Cys Val
                690                 695                 700
Lys Lys Gln Cys Pro Gln Asn Ser Gly Cys Phe Arg His Leu Asp Glu
705                 710                 715                 720
Arg Glu Glu Cys Lys Cys Leu Leu Asn Tyr Lys Gln Glu Gly Asp Lys
                725                 730                 735
Cys Val Glu Asn Pro Asn Pro Thr Cys Asn Glu Asn Asn Gly Gly Cys
                740                 745                 750
```

-continued

Asp Ala Asp Ala Lys Cys Thr Glu Glu Asp Ser Gly Ser Asn Gly Lys
            755                 760                 765

Lys Ile Thr Cys Glu Cys Thr Lys Pro Asp Ser Tyr Pro Leu Phe Asp
770                 775                 780

Gly Ile Phe Cys Ser Ser Ser Asn Phe Leu Gly Ile Ser Phe Leu Leu
785                 790                 795                 800

Ile Leu Met Leu Ile Leu Tyr Ser
            805

<210> SEQ ID NO 4
<211> LENGTH: 794
<212> TYPE: PRT
<213> ORGANISM: P. falciparum

<400> SEQUENCE: 4

Met Ser Ser Thr Ser Ser Pro Gly Asn Thr Thr Val Asn Thr Ala Gln
1               5                   10                  15

Ser Ala Thr His Ser Asn Ser Gln Asn Gln Gln Ser Asn Ala Ser Ser
            20                  25                  30

Thr Asn Thr Gln Asn Gly Val Ala Val Ser Ser Gly Pro Ala Val Val
        35                  40                  45

Glu Glu Ser His Asp Pro Leu Thr Val Leu Ser Ile Ser Asn Asp Leu
50                  55                  60

Lys Gly Ile Val Ser Leu Leu Asn Leu Gly Asn Lys Thr Lys Val Pro
65                  70                  75                  80

Asn Pro Leu Thr Ile Ser Thr Thr Glu Met Glu Lys Phe Tyr Glu Asn
            85                  90                  95

Ile Leu Lys Asn Asn Asp Thr Tyr Phe Asn Asp Asp Ile Lys Gln Phe
            100                 105                 110

Val Lys Ser Asn Ser Lys Val Ile Thr Gly Leu Thr Glu Thr Gln Lys
        115                 120                 125

Asn Ala Leu Asn Asp Glu Ile Lys Lys Leu Lys Asp Thr Leu Gln Leu
130                 135                 140

Ser Phe Asp Leu Tyr Asn Lys Tyr Lys Leu Lys Leu Asp Arg Leu Phe
145                 150                 155                 160

Asn Lys Lys Lys Glu Leu Gly Gln Asp Lys Met Gln Ile Lys Lys Leu
            165                 170                 175

Thr Leu Leu Lys Glu Gln Leu Glu Ser Lys Leu Asn Ser Leu Asn Asn
            180                 185                 190

Pro His Asn Val Leu Gln Asn Phe Ser Val Phe Phe Asn Lys Lys Lys
        195                 200                 205

Glu Ala Glu Ile Ala Gly Thr Glu Asn Thr Leu Glu Asn Thr Lys Ile
210                 215                 220

Leu Leu Lys His Tyr Lys Gly Leu Val Lys Tyr Tyr Asn Gly Glu Ser
225                 230                 235                 240

Ser Pro Leu Lys Thr Leu Ser Glu Val Ser Ile Gln Thr Glu Asp Asn
            245                 250                 255

Tyr Ala Asn Leu Glu Lys Phe Arg Val Leu Ser Lys Ile Asp Gly Lys
            260                 265                 270

Leu Asn Asp Asn Leu His Leu Gly Lys Lys Leu Ser Phe Leu Ser
        275                 280                 285

Ser Gly Leu His His Leu Ile Thr Glu Leu Lys Glu Val Ile Lys Asn
        290                 295                 300

Lys Asn Tyr Thr Gly Asn Ser Pro Ser Glu Asn Asn Lys Val Asn
305                 310                 315                 320

-continued

```
Glu Ala Leu Lys Ser Tyr Glu Asn Phe Leu Pro Glu Ala Lys Val Thr
                325                 330                 335
Thr Val Val Thr Pro Pro Gln Pro Asp Val Thr Pro Ser Pro Leu Ser
            340                 345                 350
Val Arg Val Ser Gly Ser Ser Gly Ser Thr Lys Glu Glu Thr Gln Ile
        355                 360                 365
Pro Thr Ser Gly Ser Leu Leu Thr Glu Leu Gln Gln Val Val Gln Leu
    370                 375                 380
Gln Asn Tyr Asp Glu Glu Asp Asp Ser Leu Val Val Leu Pro Ile Phe
385                 390                 395                 400
Gly Glu Ser Glu Asp Asn Asp Glu Tyr Leu Asp Gln Val Val Thr Gly
                405                 410                 415
Glu Ala Ile Ser Val Thr Met Asp Asn Ile Leu Ser Gly Phe Glu Asn
            420                 425                 430
Glu Tyr Asp Val Ile Tyr Leu Lys Pro Leu Ala Gly Val Tyr Arg Ser
        435                 440                 445
Leu Lys Lys Gln Ile Glu Lys Asn Ile Phe Thr Phe Asn Leu Asn Leu
    450                 455                 460
Asn Asp Ile Leu Asn Ser Arg Leu Lys Lys Arg Lys Tyr Phe Leu Asp
465                 470                 475                 480
Val Leu Glu Ser Asp Leu Met Gln Phe Lys His Ile Ser Ser Asn Glu
                485                 490                 495
Tyr Ile Ile Glu Asp Ser Phe Lys Leu Leu Asn Ser Glu Gln Lys Asn
            500                 505                 510
Thr Leu Leu Lys Ser Tyr Lys Tyr Ile Lys Glu Ser Val Glu Asn Asp
        515                 520                 525
Ile Lys Phe Ala Gln Glu Gly Ile Ser Tyr Tyr Glu Lys Val Leu Ala
    530                 535                 540
Lys Tyr Lys Asp Asp Leu Glu Ser Ile Lys Lys Val Ile Lys Glu Glu
545                 550                 555                 560
Lys Glu Lys Phe Pro Ser Ser Pro Pro Thr Thr Pro Ser Pro Pro Ala
                565                 570                 575
Lys Thr Asp Glu Gln Lys Lys Glu Ser Lys Phe Leu Pro Phe Leu Thr
            580                 585                 590
Asn Ile Glu Thr Leu Tyr Asn Asn Leu Val Asn Lys Ile Asp Asp Tyr
        595                 600                 605
Leu Ile Asn Leu Lys Ala Lys Ile Asn Asp Cys Asn Val Glu Lys Asp
    610                 615                 620
Glu Ala His Val Lys Ile Thr Lys Leu Ser Asp Leu Lys Ala Ile Asp
625                 630                 635                 640
Asp Lys Ile Asp Leu Phe Lys Asn Pro Tyr Asp Phe Glu Ala Ile Lys
                645                 650                 655
Lys Leu Ile Asn Asp Asp Thr Lys Lys Asp Met Leu Gly Lys Leu Leu
            660                 665                 670
Ser Thr Gly Leu Val Gln Asn Phe Pro Asn Thr Ile Ile Ser Lys Leu
        675                 680                 685
Ile Glu Gly Lys Phe Gln Asp Met Leu Asn Ile Ser Gln His Gln Cys
    690                 695                 700
Val Lys Lys Gln Cys Pro Glu Asn Ser Gly Cys Phe Arg His Leu Asp
705                 710                 715                 720
Glu Arg Glu Glu Cys Lys Cys Leu Leu Asn Tyr Lys Gln Glu Gly Asp
                725                 730                 735
Lys Cys Val Glu Asn Pro Asn Pro Thr Cys Asn Glu Asn Asn Gly Gly
            740                 745                 750
```

```
Cys Asp Ala Asp Ala Thr Cys Thr Glu Glu Asp Ser Gly Ser Ser Arg
        755                 760                 765
Lys Lys Ile Thr Cys Glu Cys Thr Lys Pro Asp Ser Tyr Pro Leu Phe
    770                 775                 780
Asp Gly Ile Phe Cys Ser Ser Ser Asn Val
785                 790
```

RECOMBINANT MALARIA VACCINE

BRIEF DESCRIPTION OF THE DRAWINGS

FIG. 3 depicts amino acid seciuences designated SEO ID NOs 1-4.

The present invention refers to a recombinant malaria vaccine and a method for its manufacture.

The merozoite surface protein (MSP-1) of the malaria parasite *Plasmodium* occurs on the surface of merozoites, the erythrocite invading form of *Plasmodium*. MSP-1 is produced as a precursor protein with a molecular weight of about 190 kDa which is proteolytically processed during merozoite maturation into four fragments designated as p83, p30, p38 and p42, which remain in a non-covalently associated form at the surface of the parasite. At the time of erythrocyte invasion, further proteolytic cleavage occurs.

The MSP-1 protein consists of several highly conserved regions, a dimorphic region associated with one of two allelic forms and of two relatively small oligomorphic blocks in the N-terminal region (Tanabe et al., J. Mol. Biol. 195 (1987) 273-287; Miller et al., Mol. Biochem. Parasitol. 59 (1993), 1-14; which are herein incorporated by reference).

There is evidence that the MSP-1 protein is a potential vaccine candidate (Holder and Freeman, Nature 294 (1981), 361-364; Majarian et al., J. Immunol., 132 (1984), 3131-3137). Further, several vaccination studies with MSP-1 material from *P. falciparum* have been carried out on primates, particularly on Aotus and Saimiri monkeys (e.g. Perrin et al., J. Exp. Med. 160 (1984), 441-451; Hall et al., Nature 311 (1984) 379-382; Siddiqui et al., Proc. Natl. Acad. Sci. USA 84 (1987), 3014-3018; Ettlinger et al., Inf. 1 mm. 59 (1991), 3498-3503; Holder et al., Parasite Immunol. 10 (1988), 607-617; Herrera et al., Proc. Natl. Acad. Sci. USA 87 (1990), 4017-4021; Herrera et al., Inf. 1 mm. 60 (1992), 154-158 and Patarroyo et al., Nature 328 (1987), 629-632, which are herein incorporated by reference).

Vaccination studies with overlapping recombinant fragments of the MSP-1 protein from *E. coli* gave protection (Tolle et al., Infect. Immun. 61 (1993), 40-47). A protective effect was also found after administration of the C-terminal domain of the MSP-1 protein in form of the p19 or p42 polypeptide (Chang et al., Inf. 1 mm. 64 (1996), 253-261). WO 98/14583 describes a method for producing a recombinant complete MSP-1 polypeptide by decreasing the AT content of the expressed DNA sequence compared to the naturally occurring sequence. There are, however, some drawbacks associated with the process described in WO 98/14583. First, the production method only allows efficient purification in the presence of N- and/or C-terminal sequence tags. Second, the purification method only works on a small scale. An adaptation to large-scale purification methods which are required in industrial processes for vaccine manufacture is not readily available.

Kauth et al. (J. Biol. Chem. 278 (2003), 22257-22264) describe the in vitro reconstitution of the MSP-1 polypeptide of *P. falciparum* strain 3D7 from heterologuously produced subunits. A purification is, however, only described for polypeptides which are fused to heterologous sequence tags such as GST, strep or hexahistidine tags. The presence of such heterologous sequences in a vaccine, however, is undesirable.

The present invention overcomes the drawbacks of the prior art by providing a composition comprising (a) a purified fragment p83/30 of the gp190/MSP-1 protein from *Plasmodium* without heterologous sequences, and (b) a purified fragment p38/42 of the gp190/MSP-1 protein from *Plasmodium* without heterologous sequences.

Preferably, the purified p83/30 fragment is an F-fragment, i.e. a fragment derived from an F-strain of *Plasmodium*, particularly from the *P. falciparum* strain FCB-1 also known as FC or F. Surprisingly, it was found that the F-fragment is more stably against proteolytic degradation than the D-fragment, i.e. a fragment derived from a D-strain of *Plasmodium*, particularly from the *P. falciparum* strain 3D7 also known as NF54. Further, it was surprisingly found that the p38/30 F-fragment may be combined with a heterologous and/or a homologous p38/42 fragment, e.g. with a heterologous p38/42 D-fragment and/or a p38/42 F-fragment.

In the composition of the invention components (a) and (b) are preferably present in about equimolar amounts, e.g. molar ratios of from 1.5:1 to 1:1.5, more preferably from 1.2:1 to 1:1.2 and most preferably from about 1:1 of component (a) to component (b).

Preferably, at least 70%, more preferably at least 80% and most preferably at least 90% of the fragments in the composition are present as non-covalently associated dimer.

Components (a) and (b) are preferably recombinant polypeptides, i.e. polypeptides which have been manufactured in a recombinant host cell, e.g. a eukaryotic host cell such as a yeast cell, e.g. *S. cerevisiae* or *P. pastoris*, or in prokaryotic cells, e.g. gram-negative bacterial cells such as *E. coli*. Preferably, the recombinant host cell is a *E. coli* cell. More preferably, the host cell is *E. coli* W3110Z2.

In a preferred embodiment, the composition of the invention has a purity of at least 95% and more, preferably of at least 97.5%, as determined by SDS gel electrophoresis and silver staining. In this context, the term "purity" refers to the absence of heterologous polypeptides, i.e. non-MSP-1 polypeptides.

In a further preferred embodiment, the composition has a content of degradation products of less than 30%, more preferably of less than 20%, and most preferably of less than 10%, as measured by SDS gel electrophoresis and immuno-staining. In this context, the term "degradation products" refers to polypeptide molecules which result from a degradation of the p83/30 fragment or the p38/42 fragment as described above.

The composition of the invention comprises a purified fragment p83/30 of the gp190/MSP-1 protein from *Plasmodium* and a purified fragment p38/42 of the gp190/MSP-1 protein from *Plasmodium*. The term "p83/30 fragment" refers to a single polypeptide comprising the p83 fragment and the p30 fragment of the MSP-1 protein of *Plasmodium*. Preferably, the composition comprises a p83/30 fragment from a *Plasmodium* F-strain. The p38/42 fragment is a single polypeptide comprising the p38 fragment and the p42 fragment of the MSP-1 protein from *Plasmodium*. The p38/42 fragment may be derived from any *Plasmodium* strain, e.g. a D-strain or an F-strain of *P. falciparum*.

The p83/30 fragment preferably comprises the amino acid sequence of an F-strain of *P. falciparum* as shown in SEQ ID NO:1 and optionally an N-terminal signal peptide sequence or a modified F-fragment derived from the F-strain sequence. In a less preferred embodiment, the p83/30 fragment comprises the amino acid sequence of a D-strain of *P. falciparum* and optionally an N-terminal signal peptide sequence or a modified D-strain sequence. The amino acid sequence shown in SEQ ID NO:2 is derived from the amino acid sequence of a D-strain and comprises 2 amino acid substitutions at position 611 (E→K) and 866 (Q→H).

The p38/42 fragment may be derived from an F-strain of *P. falciparum* as shown in SEQ ID NO:3 and/or from a D-strain of *P. falciparum* as shown in SEQ ID NO:4. Surprisingly, it was found that a p83/30 fragment of an F-strain may be both combined with a homologous p38/42 fragment from an F-strain or with a heterologous p38/42 fragment from a different *P. falciparum* strain, e.g. a D-strain.

The terms "p83/30 fragment" and "p38/42 fragment" also refer to modified fragments which have an amino acid sequence identity of at least 90%, preferably of at least 95% and more preferably of at least 98% over the entire length of the polypeptide to a native p83/30 or p38/42 fragment. The terms also encompass truncated fragments which may comprise deletions of single amino acids and/or amino acid portions of up to 10, more preferably up to 5 amino acids compared to the wild-type polypeptide. A p83/30 fragment preferably has a length of at least 800 amino acids, more preferably of at least 850 amino acids. Further, the p83/30 fragment has a sequence identity of at least 90%, more preferably at least 95% and, most preferably, at least 98% with the p83/30 fragment of the *P. falciparum* F-variant in SEQ ID NO:1.

The p38/42 fragment preferably has a length of at least 700 amino acids and more preferably at least 750 amino acids. Further, it is preferred that the p38/42 fragment has a sequence identity of at least 90%, more preferably at least 95% and, most preferably, at least 98%, compared to the p38/42 fragments from a *P. falciparum* F-strain (SEQ ID NO:3) and/or from a D-strain (SEQ ID NO:4).

The amino acid sequence of particularly preferred embodiments of p83/30 and p38/42 are shown in SEQ ID NO:1, 2, 3 and 4.

The present invention also refers to a pharmaceutical preparation comprising a composition as described above and pharmaceutically acceptable carriers, diluents and/or adjuvants. Preferably, the preparation is a vaccine.

The vaccine may be present as reconstitutable lyophilisate, as liquid, e.g. as solution or suspension, or as emulsion, e.g. as water-in-oil emulsion. The vaccine may comprise adjuvants such as alum, MF59 or BCG, including recombinant BCG as disclosed in PCT/EP2005/011127, "Combination of a bacterial cell and a biologically active agent" which is herein incorporated by reference. The vaccine is preferably administered by injection, e.g. intradermal, subcutaneous or intramuscular injection.

A preferred dosage of the vaccine comprises 1-500 µg, more preferably 20-100 µg protein for application in human medicine. The vaccine may be administered in a single dose or in multiple doses. The administration in multiple doses is preferred.

The composition of the present invention may be manufactured by a process comprising the steps
(a) expressing the fragment p83/30 of the gp190/MSP-1 protein from *Plasmodium* without heterologous sequences in a host cell,
(b) expressing the fragment p38/42 of the gp190/MSP-1 protein from the *Plasmodium* without heterologous sequences in a host cell,
(c) recovering the fragment p83/30 and the fragment p38/42 from the host cells,
(d) optionally combining the fragments p83/30 and p38/42, and
(e) purifying the combined fragments.

The expression of the fragments p83/30 and p38/42 may be carried out in a single host cell or separately in a first host cell and in a second host cell. The use of separate first and second host cells is preferred. The host cell may be provided by transfection with a nucleic acid encoding the respective MSP-1 fragment. Preferably, the nucleic acid encoding the p83/30 fragment and the nucleic acid encoding the p38/42 fragment may be located on an expression vector suitable for the respective host cell, e.g. a gram-negative bacterial cell such as an *E. coli* cell. The expression vector may be an episomal vector such as a plasmid, or a chromosomally integrated vector. The expression vector comprises the nucleic acid in operative linkage with a suitable expression control sequence, e.g. which may comprise a constitutive or an inducible promoter. The expression vector may comprise further genetic elements, e.g. an origin of replication, a selection marker etc. Examples of suitable expression vectors are disclosed in Sambrook et al., Molecular Cloning, A Laboratory Manual (1989), Cold Spring Harbor Laboratory Press, and other standard text books.

When the host cells are bacterial cells, e.g. *E. coli* cells, the fragments are preferably expressed in insoluble form, e.g. as inclusion bodies. Preferably, the fragments are separately recovered as inclusion bodies which may be separately solubilized, e.g. in the presence of chaotropic salts such as guanidinium hydrochloride and subsequently refolded, e.g. in the presence of arginine and thiol reagents such as glutathione. Alternatively, the p83/30 and p38/42 fragments may be combined before solubilization, after solubilization or after refolding in a suitable molar ratio. After refolding, the fragments are transferred to a suitable buffer which may comprise a non-ionic surfactant such as Tween 80, Tween 20 or Triton X-100. If desired, the fragments may be separately purified by subsequent processing steps, comprising at least one of the following: filtration, anion and/or cation exchange chromatography such as Q-sepharose HP-chromatography, or SP-sepharose HP-chromatography, conditioning and concentration, e.g. by ultrafiltration.

According to step (d), the fragments are combined. Preferably, the fragments are combined in about equimolar amounts as indicated above. The amount of the respective fragment may be determined by spectroscopic protein measurements, e.g. by determining UV absorption at 280 nm. It is especially preferred that the fragments are combined in the absence of heterologous polypeptides such as albumin.

After combining, the fragments may be further purified, e.g. by size exclusion chromatography, e.g. using Sephacryl S 300-HR/GE. Further treatments may comprise filtration, concentration and sterilisation, e.g. by sterile filtration.

The nucleic acids encoding the fragments p83/30 and p38/42 may have a reduced AT content compared to the wild type sequence as described in WO 98/14583, which is herein incorporated by reference.

Further, the invention refers to a composition comprising a purified fragment p83/30 of the gp190/MSP-1 protein from a *Plasmodium* F-strain. The p83/30 fragment preferably comprises the sequence as shown in SEQ ID NO:1 or a modified sequence as described above. This composition is preferably used as a pharmaceutical preparation, e.g. as a vaccine as described above. With regard to the preferred characteristics, e.g. purity and/or content of degradation products, of this composition, it is referred to the disclosure as described above.

The present invention shall be explained by the following examples:

EXAMPLE 1

Manufacture of the p83/30 Fragment

Figure 1:
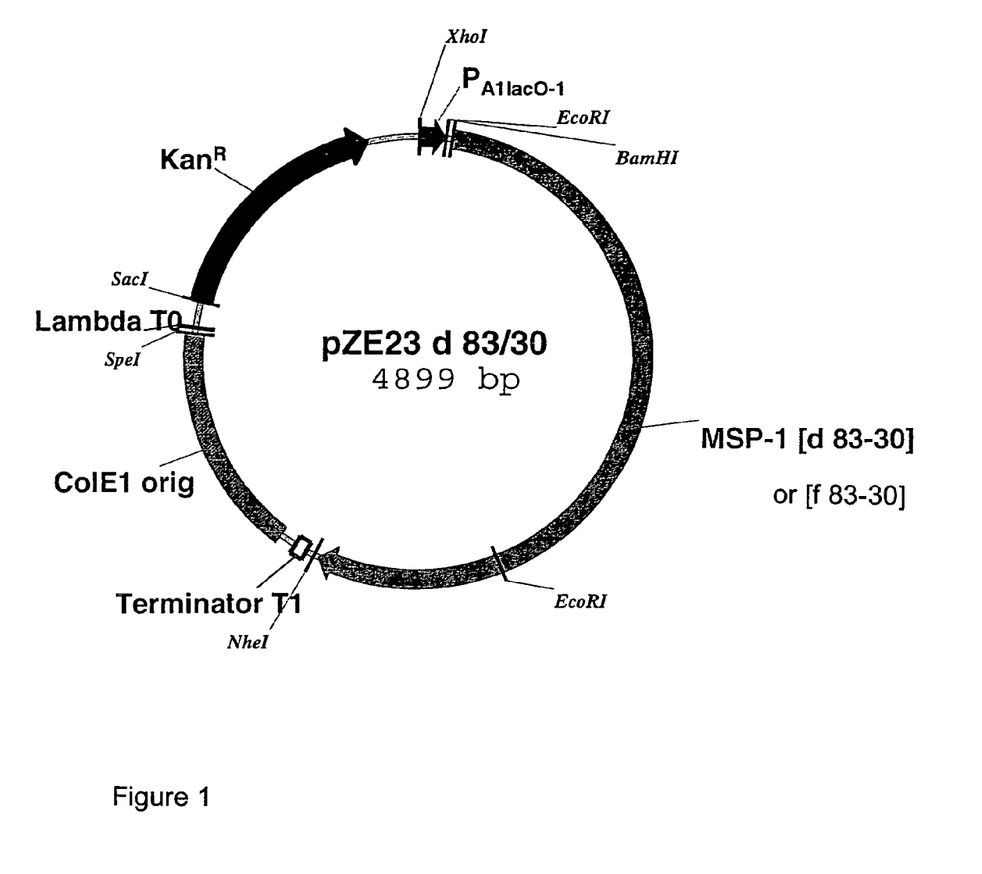
FIG. 1 depicts the expression vector pZE23D.

The amino acid sequence of the p83/30 fragment is shown in SEQ ID NO:1 (F-strain) or SEQ ID NO:2 (D-strain). A nucleic acid sequence encoding such a fragment was cloned into the expression vector pZE23D 83/30 shown in FIG. 1. The fragment encoding nucleic acid is operatively linked with the IPTG-inducible pA1lacO1 promoter. The *E. coli* production strain was W3110Z2 (e.g. Bacteriol. Ref. 36, (1972), 525-530; Proc. Natl. Acad. Sci. USA 78 (1981), 7069-7072).

The *E. coli* cells were pre-cultured in LB medium. The pre-culture was diluted 1:50 with Superbroth and cultivated in a fermenter at 37° C. At an optical density ($OD_{600}$) of 1.5, doxycycline (200 ng/ml) was added. At $OD_{600}$=4.5, IPTG (1 mM) was added.

The cells were harvested at an $OD_{600}$=7 or 2.5 h after induction with IPTG.

The harvested bacteria were disrupted by continuous homogenization at a turn over rate of 10 l/h and 1500 bar maximal pressure (Niro-Soavi, Type Panda). The homogenate was centrifuged for 30 min at 6000 g followed by two wash/centrifugation cycles in order to obtain the inclusion bodies.

Figure 2:
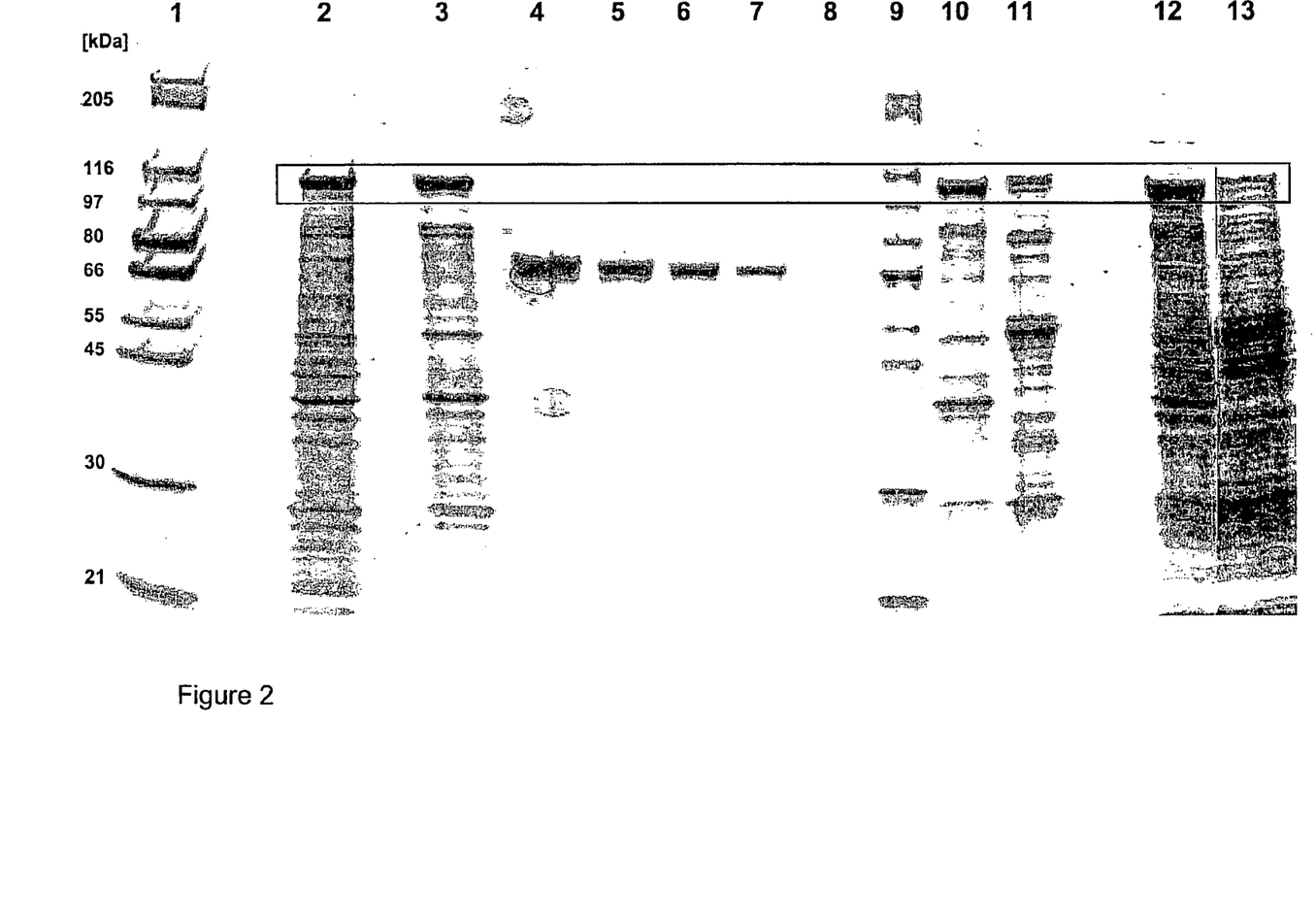
FIG. 2 depicts a comparison of the stability of inclusion bodies of the p83/30 fragment from a D- and an F-strain.

A comparison of the stability of inclusion bodies of the p83/30 fragment from a D- and an F-strain is shown in FIG. 2. The lanes on the figure are as follows:
1+9: marker;
2: fermentation sample of F-83/30;
3: IBs F-83/30 after preparation;
4: bovine serum albumin (BSA) 800 ng;
5: BSA 600 ng;
6: BSA 400 ng;
7: BSA 200 ng;
8: BSA 100 ng;
10: IBs F-83/30 (after storage for 9 months at −18° C.);
11: IBs of D-83/30 (after preparation);
12: fermentation sample of F-83/30;
13: fermentation sample of D-83/30.

It is evident from FIG. 2 that the p83/30 fragment of a *P. falciparum* F-strain is significantly more stable than the corresponding p83/30 fragment from a D-strain.

EXAMPLE 2

Manufacture of the p38/42 Fragment

The amino acid sequence of the p38/42 fragment is shown in SEQ ID NO:3 (F-strain) or SEQ ID NO:4 (D-strain).

Inclusion bodies of the p38/42 fragment were produced substantially as described in Example 1 for the p83/30 fragment.

EXAMPLE 3

Manufacture of a Composition Comprising Equimolar Amounts of p83/30 and p38/42 Fragment The inclusion bodies obtained in Examples 1 and 2 were separately solubilized by adding solubilization buffer (6 M guanidinium HCl; 50 mM Na phosphate; 10 mM dithiotreitol, 1 mM EDTA, pH 8.0) to the Inclusion Bodies (IBs).

For the p83/30 fragments, three different ratios of IBs to solubilization buffer were used, namely 1 g IB+2.5 ml buffer; 1 g IB+4.0 ml buffer and 1 g IB+8.0 ml buffer. For the p38/40 fragment, 1 g IB were added to 2.5 ml buffer.

The filtrate was subjected to a refolding procedure by incubation in 500 mM arginine, 50 mM Na phosphate, 1 mM L-glutathione reduced, 0.1 mM glutathione oxidized, 1 mM EDTA pH 8.0 overnight at room temperature.

The resulting protein solutions were 5× concentrated by ultrafiltration. The buffer was exchanged with 20 mM Na phosphate, 50 mM NaCl, 0.01% Tween 80 pH 8.0. After filtration in a 0.2 μm filter, the product was subjected to Q-sepharose HP chromatography. The elusion took place in a 0-100% gradient of buffer A (20 mM Na phosphate, 50 mM NaCl, 0.01 Tween 80 pH 8.0) and buffer B (20 mM Na phosphate, 350 mM NaCl, 0.01% Tween 80 pH 8.0).

The eluates were conditioned by dilution 1:5 in dilution buffer (10 mM Na phosphate, 0.01% Tween 80 pH 5,8) and filtered through a 0.2 μm filter. The resulting product was subjected to an SP sepharose HP chromatography and eluted in a gradient of 0-100% of buffer A (10 mM Na phosphate, 50 mM NaCl, 0.01% Tween 80, pH 5.8) and buffer B (10 mM Na phosphate, 600 mM NaCl, 0.01% Tween 80, pH 5.8). Subsequently, the pH was adjusted to 7.4.

The protein solutions were concentrated to 4 mg/ml by ultrafiltration. Then, both subunits were pooled in a ratio of 1:1 (based on total protein amounts measured by UV at 280 nm) in the absence of heterologous polypeptides. After filtration, the composition was subjected to size exclusion chromatography, e.g. with Sephacryl-S-300 HR/GE in 1×PBS buffer pH 7.2-7.4. The composition was optionally concentrated by ultrafiltration in order to provide a concentration of up to 1 mg protein/ml. After sterile filtration, the composition was stored.

The invention claimed is:

1. A composition comprising
   (a) a purified fragment p83/30 of the gp190/MSP-1 protein without heterologous sequences, wherein the p83/30 fragment is from *Plasmodium falciparum* strain FCB-1; and
   (b) a purified fragment p38/42 of the gp190/MSP-1 protein without heterologous sequences, wherein the p38/42 fragment is from a *Plasmodium falciparum* strain other than FCB-1.

2. The composition of claim 1, wherein component (b) is a p38/42 fragment from a D-strain of *Plasmodium*.

3. The composition of claim 2, wherein component (b) is a p38/42 fragment from *Plasmodium falciparum* strain 3D7.

4. The composition of claim 1, wherein components (a) and (b) are present in about equimolar amounts.

5. The composition of claim 1, wherein components (a) and (b) are recombinant polypeptides.

6. The composition of claim 1 which has a content of degradation products of less than 30%.

7. The composition of claim 1 which has a content of degradation products of less than 20%.

8. The composition of claim 1 which has a purity of at least 95%.

9. The composition of claim 1 which has a purity of at least 97.5%.

10. A pharmaceutical preparation comprising: a) a composition of claim 1; and b) one or more of a pharmaceutically acceptable carrier, a pharmaceutically acceptable diluent, and a pharmaceutically acceptable adjuvant.

11. The pharmaceutical preparation of claim 10 which is a vaccine.

12. A method for manufacturing the composition of claim 1, the method comprising the steps:
   (a) expressing the fragment p83/30 of the gp190/MSP-1 protein from *Plasmodium* without heterologous sequences in a host cell,
   (b) expressing the fragment p38/42 of the gp190/MSP-1 protein from *Plasmodium* without heterologous sequences in a host cell,
   (c) recovering the fragment p83/30 and the fragment p38/42 from the host cells,
   (d) combining the fragments p83/30 and p38/42, and
   (e) purifying the combined fragments.

13. The method of claim 12 wherein the fragments p83/30 and p38/42 are expressed in the same host cell.

14. The method of claim 12 wherein the fragments p83/30 and p38/42 are expressed in different first and second host cells.

15. The method of claim 12, wherein the host cell is a bacterial cell.

16. The method of claim 15, wherein the bacterial cell is a gram-negative bacterial cell.

17. The method of claim 16, wherein the bacterial cell is an *E. coli* cell.

18. The method of claim 15, wherein the host cell is an *E. coli* W3110Z2 cell.

19. The method of claim 12, wherein the fragments are separately recovered as inclusion bodies.

20. The method of claim 12, wherein the inclusion bodies are separately solubilized.

21. The method of claim 12, wherein the solubilized fragments are separately refolded.

22. The method of claim 12, wherein the fragments are combined in about equimolar amounts.

23. The method of claim 12, wherein the combined fragments are purified by size exclusion chromatography.

* * * * *